(12) United States Patent
Robinson

(10) Patent No.: US 6,370,414 B1
(45) Date of Patent: Apr. 9, 2002

(54) SYSTEM AND METHOD FOR MEASURING, ESTIMATING AND DISPLAYING RMS CURRENT DENSITY MAPS

(75) Inventor: Stephen E. Robinson, Maple Ridge (CA)

(73) Assignee: CTF Systems, Inc., Port Coquitlam (CA)

(*) Notice: Subject to any disclaimer, the term of this patent is extended or adjusted under 35 U.S.C. 154(b) by 0 days.

(21) Appl. No.: 09/600,730
(22) PCT Filed: Jan. 20, 1999
(86) PCT No.: PCT/CA99/00044
§ 371 Date: Jul. 20, 2000
§ 102(e) Date: Jul. 20, 2000
(87) PCT Pub. No.: WO99/37206
PCT Pub. Date: Jul. 29, 1999

Related U.S. Application Data (60) Provisional application No. 60/072,340, filed on Jan. 23, 1998.

(51) Int. Cl.[7] .................................. A61B 5/05
(52) U.S. Cl. .................. 600/409; 382/128; 324/301; 324/302; 324/244; 324/260; 324/248
(58) Field of Search ................... 600/407, 409, 600/345, 373, 374, 378, 425; 324/300, 301, 302, 248, 244, 260, 262; 382/128

(56) References Cited

U.S. PATENT DOCUMENTS

| | | |
|---|---|---|
| 4,947,480 A | 8/1990 | Lewis |
| 4,949,725 A | 8/1990 | Raviv et al. |
| 4,977,896 A | 12/1990 | Robinson et al. |
| 5,136,242 A | 8/1992 | Abraham-Fuchs |

(List continued on next page.)

FOREIGN PATENT DOCUMENTS

| | | |
|---|---|---|
| DE | 4218563 A | 2/1993 |
| DE | 4326041 | 4/1994 |
| DE | 4326043 | 4/1994 |
| DE | 4326044 | 4/1994 |
| EP | 406963 A | 1/1991 |
| EP | 504027 A | 9/1992 |
| JP | 5-015504 | 1/1993 |
| JP | 6-245916 | 9/1994 |
| WO | WO 94/12100 | 6/1994 |
| WO | WO 96/41209 | 12/1996 |

OTHER PUBLICATIONS

Walter H. Kullmann, "Biomagnetic Imaging", IEEE Engr. in Medicine & Biology 10th Annual Intl. Conf., New Orleans, Nov. 4–7, 1988, pp. 439–440.

Primary Examiner—Marvin M. Lateef
Assistant Examiner—Jeoyuh Lin
(74) Attorney, Agent, or Firm—Merchant & Gould PC (57) ABSTRACT

A method of performing synthetic aperture magnetometery on the signals from a target organ using an array of biomagnetic sensors positioned in a predetermined manner around the target organ, each sensor in the array having a position vector and an orientation vector relative to a common coordinate system encompassing the target organ. The method includes the steps of: simultaneously measuring EM signals from each sensor positioned in the array for a selected time interval; computing a covariance matrix of the measured EM signals over a user-selected time sub-interval within the selected time interval; selecting a set of coordinates for a region of interest to be imaged and a distance between voxels to form a grid of voxels; computing a forward solution for a current element at each of the voxels for each of the sensors in the array sensors; computing an RMS current density estimate for each voxel from the covariance matrix and the forward solution for that voxel; and displaying the voxels estimating RMS current density as a first image. The method is particularly well suited for evaluating brain activity in a human subject.

14 Claims, 4 Drawing Sheets

U.S. PATENT DOCUMENTS

| | | |
|---|---|---|
| 5,170,119 A | 12/1992 | Sekihara et al. |
| 5,228,443 A | 7/1993 | Tatar |
| 5,263,488 A | 11/1993 | Van Veen et al. |
| 5,269,325 A | 12/1993 | Robinson et al. |
| 5,285,385 A | 2/1994 | Igarshi et al. |
| 5,307,807 A | 5/1994 | Valdes Sosa et al. |
| 5,315,308 A | 5/1994 | Nehorai et al. |
| 5,392,210 A | 2/1995 | Scholz |
| 5,417,211 A | 5/1995 | Abraham-Fuchs et al. |
| 5,426,365 A | 6/1995 | Sekihara et al. |
| 5,511,008 A | 4/1996 | Flament et al. |
| 5,524,086 A | 6/1996 | Kiyuna |
| 5,526,811 A | 6/1996 | Lypchuk |
| 5,594,849 A | 1/1997 | Kuc et al. |
| 5,601,081 A | 2/1997 | Tomita et al. |
| 5,655,534 A | 8/1997 | Ilmoniemi |
| 5,671,740 A | 9/1997 | Tomita et al. |
| 5,682,889 A | 11/1997 | Tomita et al. |
| 5,687,724 A | 11/1997 | Jewett et al. |
| 5,701,909 A | 12/1997 | Amir et al. |
| 5,730,131 A | 3/1998 | Ohyu |
| 5,752,514 A | 5/1998 | Okamura et al. |
| 5,755,227 A | 5/1998 | Tomita et al. |
| 5,794,620 A | 8/1998 | Dossel et al. |
| 5,885,215 A | 3/1999 | Dossel et al. |

$r_i$: sensor position vector
$u_i$: sensor orientation vector
$r_0$: source position vector
$j_0$: source current vector
NAS: nasion
LPA: left pre-auricular point
RPA: right pre-auricular point

SYSTEM AND METHOD FOR MEASURING, ESTIMATING AND DISPLAYING RMS CURRENT DENSITY MAPS

This Application is 371 of PCT/CA99/00044 filed Jan. 20, 1999 which claims benefit of Ser. No. 60/072,340 filed Jan. 23, 1998.

TECHNICAL FILED

The present invention relates to the measurement and analysis of bioelectro-magnetic activity in electrically active organs. More specifically, the present invention relates to a method of transforming the measurements into a corresponding current distribution map estimating the original sources and combining current distribution maps of two or more states of organ activity into difference maps that reveal regions of the organ in which activity differs for the different states.

BACKGROUND

The ion currents of electrically active organs such as the brain and heart can generate magnetic fields that can be measured outside the surface of the body. Further, the corresponding electrical potentials in the organs themselves, when conducted through the body, can be measured on the skin, using surface electrodes or in the interior of the body by means of invasive depth electrodes. The process of computing the biological source current or currents giving rise to the observed magnetic and electrical measurements is generally referred to as "the bioelectromagnetic inverse problem". The importance of having a biomagnetic or bioelectric inverse solution is that it can be used to correlate electrophysiological function with a particular coordinate within the body. This, in turn, can be used to associate normal function and dysfunction with specific anatomic structures. It can be shown that, in three dimensions, there can be no unique bioelectromagnetic inverse solution without applying constraints to the solution, such as assuming the number and configuration of possible sources. Notwithstanding this, it is possible to calculate useful estimates or approximations of the distribution and intensity of source activity from electrophysiological measurements.

In the present art, Magnetoencephalographic (MEG) and Electroencephalographic (EEG) signals may be examined for waveform morphology in independent channels, characterized, for example, by their frequency and amplitude. In addition, MEG and/or EEG measurements, recorded from a plurality of sites, are often represented as topographic distributions of either spontaneous or evoked signals in the form of signal intensity maps about the head. Such topographic maps are also commonly presented for MEG/EEG in distinct frequency bands.

It is also known to average MEG and EEG signals synchronously with a stimulus presented to the subject or to a voluntary motor movement from the subject. Signal averaging can improve the signal-to-noise ratio (SNR) of the brain activity underlying a particular sensory or motor event. The resulting averaged signal is conventionally known as the event-related potential (ERP) or the event-related field (ERF). The averaged evoked response is most useful for improving the SNR or activity in the primary cerebral cortex, in which the time delay between stimulus and response has low variability. However, the evoked response relating to higher cognitive functions, which involve associative cerebral cortex, can be more variable in time delay and duration relative to the driving stimulus. Thus, signal averaging is less useful for evaluating higher cognitive functions. The application of signal averaging to EEG and MEG brain signals is predicated upon the notion that the underlying neural events are identical with each and every stimulus event. Common sense and personal experience dictate that this is not necessarily the case for higher levels of brain functioning. The delay between external events and related thought processes is known to vary greatly. Brain activity associated with critical higher mental processes, such as the production and understanding of language, are therefore not adequately represented by the averaged evoked response.

Another known representation of the MEG and EEG signals is the Equivalent Current Dipole (ECD). The ECD can be computed by fitting a simplified model of a current dipole (or multiple dipoles), each characterized by a location, current vector, and magnitude, to the MEG and/or EEG measurements at some selected instant of time, usually in the least squares sense. In the Minimum Norm Current Distribution method, a more complex, often underdetermined model is fitted to the measurements at some instant of time by a least squares method. Both the ECD and Minimum Norm methods can yield erroneous results (e.g., inaccurate localization and magnitude of cortical generators) when noise is present in the EEG or MEG signal. When the Minimum Norm solution is underdetermined (and it almost always is), the non-uniqueness of the inverse problem implies that the result is only one of many possible source configurations that can explain the measurements. Thus, only spontaneous EEG or MEG signals having high signal-to-noise ratio and a source characterized by few parameters, such as epileptic spikes and abnormal high-amplitude "slow waves" (a sign of closed-head injury) can be localized accurately by these two methods. Normal (non-pathological) events within the brain are of much lower amplitude; when possible, signal averaging is conventionally used to improve the signal-to-noise ratio of such events.

Much of the above-mentioned prior art is described in SQUID-Based Measuring Techniques by Manfried Hoke in THE ART OF MEASUREMENT METROLOGY IN FUNDAMENTAL AND APPLIED PHYSICS, edited by B. Kramer (1988).

The activity of electrically active organs, such as the brain, may also be monitored and imaged using Positron Emission Tomography (PET) and fictional magnetic resonance imaging (fMRI). Neither of these imaging modalities are direct measures of the electrochemical events that comprise neural activity. Instead, they detect local changes in metabolism, metabolic products or blood flow within the brain. These changes are consequent to the energy requirements of the electrochemical events. Although electrochemical events can occur in less than one millisecond, corresponding local changes in metabolism and blood flow are much slower, having time constants of several seconds. Hence, PET and fMRI lack the time resolution of EEG and MEG, as they are indirect measures of brain activity.

Lead Field Synthesis (LFS) departs from previous methods for analyzing bioelectromagnetic measurements. LFS is disclosed by S. E. Robinson and W. C. Black in U.S. Pat. No. 4,977,896 (Robinson et al.) and U.S. Pat. No. 5,269,325 (Robinson et al.) entitled "Analysis of Biological Signals using Data from Arrays of Sensors". Instead of localizing brain activity, LFS increases the spatial selectivity of an array of MEG sensors by summing the weighted observations. The weights are selected to impart higher spatial selectivity to a specified coordinate in the head. The sum of products of the measured signal and these weights results in a "virtual sensor" that estimates electrical activity as a function of time at the selected location.

It is also known that the bioelectromagnetic inverse solution can be improved by constraining the location of source currents to the cortex of the brain, since it is the electrical currents flowing between the dendrites and cell bodies of the neurons that are the primary contributors to the measured magnetic fields and electrical potentials. Furthermore, the source current is known to flow in a direction approximately normal to each point on the cortical surface which provides an additional constraint for the inverse solution. The coordinates and vectors describing the cortical surface can be extracted from anatomical images of the brain. These images can be obtained, for example, using magnetic resonance imaging (MRI) or computed tomography (CT) scanning of the head.

While certain advances have been made in this art, there is still much room for improvement. For example, heretofore, the prior art approach has been unable to localize brain activity in a manner which can adequately represent spontaneous (unaveraged) activity (e.g., brain activity), particularly that of normal higher cognitive functions.

Specifically, certain prior art approaches (e.g., the ECD and Minimum Norm methods discussed above) rely on "model-fitting" techniques generally involving the following steps:

(i) the signals are initially observed at some instant or time sample;

(ii) a parametric model is used to predict a forward solution for the measurements; and (iii) the parameters of the model are adjusted so as to simultaneously minimize the differences between measured and predicted signals at each of the sensors—usually in the least-squares sense.

As an example, a single ECD may be described using five free parameters for magnetic measurements—three for position, one describing the tangential dipole-moment vector (radial currents are "silent" in magnetic measurement) and one describing the dipole-moment magnitude. Further, for ECD representation to be operable, a relatively high signal-to-noise (SNR) ratio is needed. However, for certain organs such as the brain, the spontaneous signals generated by small functional regions do not provide an adequate SNR ratio (in the case of the brain, this is due to the fact that brain functions are also being carried out in areas which are not of interest). Accordingly, it is necessary to use signal averaging techniques to improve the SNR ratio. For signal averaging techniques to be useful, it is necessary that the regions of interest in, for example, the brain are in precise synchrony with external events resulting in poor vision of associative areas. Accordingly, practical imaging of high brain function from MEG and EEG signals has heretofore been at least difficult (if not possible) to achieve. In the Minimum Norm solutions, there are many times more free parameters. When there are more parameters than sensors (measurements) the problem becomes underdetermined.

Certain other prior art approaches (e.g., the LFS method discussed above) rely generally involve the following steps (i) the signals are initially observed;

(ii) observed signals are weighted by some coefficient; and (iii) derivation of an additional signal which is an estimate of activity (e.g., brain activity).

This approach has limited value in evaluating higher cognitive functions due to the rapid fluctuations (liability) of the activity of certain organs (e.g., the brain).

It would be desirable to have a system and method for measuring, estimating and displaying root mean square (RMS) current density maps which obviates or mitigates the above-mentioned limitations of the prior art.

SUMMARY OF THE INVENTION

It is an object of the present invention to provide a novel apparatus and method for measuring, estimating, and displaying RMS current density maps of brain activity which obviates or mitigates at least one of the disadvantages of the prior art methods for calculating estimates of the distribution and intensity of source activity from electrophysiological measurements.

The system and method of the present invention, referred to herein as Synthetic Aperture Magnetometery (SAM) methodology, permits tomographic imaging of brain activity and represents a radical departure from the previously described prior art methods for analysing MEG and/or EEG data. In contrast to the conventional methods (e.g., ECD, minimum norm and LFS taught in Robinson et al. patents), SAM converts the measured data from, for example when brain activity is being evaluated, an MEG and/or EEG sensor array over a segment of time (rather than at a single instant), into an estimate of the RMS source current density at any designated location in the head. The present invention also provides, in the example of evaluating brain activity, a method for displaying the brain activity that differs between two or more states of brain activity. This latter process is referred to herein as Differential Current Density Mapping (CDM). In applying DCDM, individual SAM images are derived from MEG and/or EEG data which has been partitioned into discrete time segments. The time segments correspond to at least two mental states under examination. The SAM image derived for each mental state are then combined using DCDM to display the locations and intensities of the brain that differ between the at least two mental states, Since the common mode brain activity is attenuated by the subtraction process, the locations and interactions of the brain activity that differ between any two brain states is readily identified.

Accordingly, in one aspect of the present invention, there is provided a method of performing synthetic aperture magnetometery on the signals from a target organ using an array of biomagnetic sensors positioned in a predetermined manner around the target organ (e.g., the brain), each sensor in the array having a position vector and an orientation vector relative to a common coordinate system encompassing the target organ (e.g., the brain), the method comprising the steps of:

(i) simultaneously measuring EM signals from each sensor positioned in the array for a selected time interval;

(ii) computing a covariance matrix of the measured EM signals over a user-selected time sub-interval within the selected time interval;

(iii) selecting a set of coordinates for a region of interest to be imaged and a distance between voxels to form a grid of voxels;

(iv) computing a forward solution for a current element at each of the voxels for each of the sensors in the array sensors;

(v) computing an RMS current density estimate for each voxel from the covariance matrix and the forward solution for that voxel; and (vi) displaying the voxels estimating RMS current density as a first image. This method is typical of SAM.

Thus, in the present method, as will be illustrated below, when reference is made to positioning of biomagnetic sensors in a predetermined manner around a target organ, those of skill in the art will appreciate that this means that the sensors are placed in the vicinity of the target organ, usually external to the surface of the body. As is known in the art, the sensitivity of biomagnetic sensors declines rapidly with distance (inverse cube law for simple magnetometers, inverse 4th power for first-order gradiometers, etc.). Also, the fine (i.e., "higher-order") spatial features of the biomagnetic field, necessary for distinguishing different sources, also decline with distance. This means that the biomagnetic sensors must be placed as close to the body as is practically feasible. Ideally, biomagetic sensors of a number sufficient to obtain as many different "perspective" measurements as is possible are placed around or in the vicinity of the target organ. Further, the common coordinate system encompassing the target organ is related to the position vector and orientation vector of each sensor in the array. The magnetic field of the target organ (e.g., the brain, as well as other organs), is a vector quantity. The features of such a field convey information as to the location and intensity of each of the cortical generators (sources). The field should be sampled, spatially, at small enough intervals, surrounding as much of the target organ as possible, to convey information needed for localization and imaging.

As used throughout this specification, the term "EM signals" is intended to mean the signals generated from ion currents in electrically active organs. Generally, these signals will be bioelectric signals, biomagnetic signals or a combination of these. Thus, if the electrically active organ is a brain the EM signals can be magnetoencephalogram (MEG) signals, electroencephalogram (BEG) signals or a combination of these. Alternatively, if the electrically active organ is a heart the EM signals can be electrocardiogram (ECG) signals, magnetocardiogram (MCG) signals or a combination of these. Further alternatively, if the electrically active organ is an eye, the EMG signals can be electrooculogram (EOG) signals, magnetooculogram (MOG) signals or a combination of these. Persons of skill in the art will recognize that the precise nomenclature of the EM signals useful in the present method will depend on the particular target organ.

Further, as used throughout this specification, the term "forward solution" is intended to mean a computation of the magnetic field or electrical potential response of a mathematically modelled sensor or electrode to a mathematically modeled current distribution within a mathematically modeled conducting volume. As will be understood by those of skill in the art, closed mathematical solutions exist for a unique forward solution of signal from source. By contrast, there is no closed and unique mathematical solution for the bioelectromagnetic inverse. Hence, all inverse solutions rely upon forward solutions. More information on forward solutions may be found in *Basic Mathematical and Electro magnetic Concepts of the Biomagnetic Inverse Problem* by J. Sarvas (Phys. Med. Biol. 32:11-22 (1987)).

Preferably, the method includes repeating Steps (ii) through (vi) over a second time sub-interval within the selected time interval, to produce a second RMS current density image and, the additional step of subtracting the second RMS current density image, voxel by voxel, from the first image to form a third RMS current density image representing the difference source activity in the brain between the first and second time windows. This preferred embodiment is typical of DCDM.

DESCRIPTION

The method of the present invention, conveniently referred to herein as Synthetic Aperture Magnetometery (SAM) methodology, generally resembles techniques previously employed for forming synthetic aperture antenna arrays, as used in radio. In synthetic aperture methods, an array of antennas can be combined into a much more directional antenna than any of its individual elements taken alone. The present inventor notes that, while the method of the present invention may be used advantageously in magnetometery and magnetoencephalographic (MEG) data measurement, the method may also be used in electroencephalographic (EEG) data measurements or even in a combination of MEG and EEG data measurement. While the bulk of this specification is directed to describing how SAM methodology can be used to measure magnetic signals from the brain, it will be readily understood by those of skill in the art that the method of the present invention is applicable to any electrical and/or magnetic measurements from any electrically active organ of the body, including but not limited to: the heart, nerves, smooth muscle, skeletal muscle and secretory organs. While MEG and EEG data measurement is specifically suited to electrophysiological data measurement of the brain, signal data from other electrically active organs may also be used in the present method. As discussed above, the nomenclature for signals underlying such data will depend on the particular target organ. For much of this specification, and to facilitate an understanding of the present method, the context of this disclosure is directed, but not limited to, MEG data measurement.

When SAM is applied to measurements from a sensor array formed from a plurality of MEG and/or EEG sensors, the spatial selectivity of the sensor array to source activity can be much greater than that of the individual sensors. The results of the method of the present invention displays an estimate of the source activity in the form of images of the intensity versus location of the brain's electrical activity, as known to those of skill in the art as being encompassed by "Functional Neuroimaging". Functional neuroimaging conventionally has been used primarily with PET, fMRI and single photon emission computed tomography (SPECT)— see, for example, "Functional Neuroimaging" (subtitle: Technical Foundations) ISBN:0126858454, Editors: Thatcher et al, Academic Press (1994). Accordingly, these images showing the distribution of brain activity in both healthy and diseased states may be employed directly as a medical diagnostic tool. However, since the normal brain is active to varying degrees through-out its entire volume, it is often difficult to discern the activity of centers relating to specific faculties such as speech, emotion, and other higher cognitive functions. Therefore, by having the subject presented with stimuli or perform tasks that preferably differ by only one quality, an image of each activity state can be produced. The images are then subtracted from each other to remove the common-mode brain activity. The result of this method reveals images of the brain activity representative of the selected cognitive state.

As an example, the MEG of a subject might be measured while reading a story containing additional unreadable words, presented one word at a time or tachistoscopically. Two SAM images can then be created from the measurements of the brain activity: one image illustrating brain activity during perception of the words of the story; and the second illustrating brain activity during perception of the unreadable words. By subtracting these two images of brain activity, a third "difference image" is derived for which the activity common to both states or the "common-mode" brain activity is removed. By representing the brain activity by a difference image, one can then localize where in the brain reading activity takes place.

Accordingly, the SAM method, which permits tomographic imaging of brain activity, represents a radical departure from the conventional previously described prior art methods for analysing MEG and/or EEG signals. In contrast to the conventional methods, SAM converts the data measurements of the sensor array over a user selected time window rather than at a single instant in time, into an estimate of the RMS source current density at any designated location in the brain.

Figure 1:
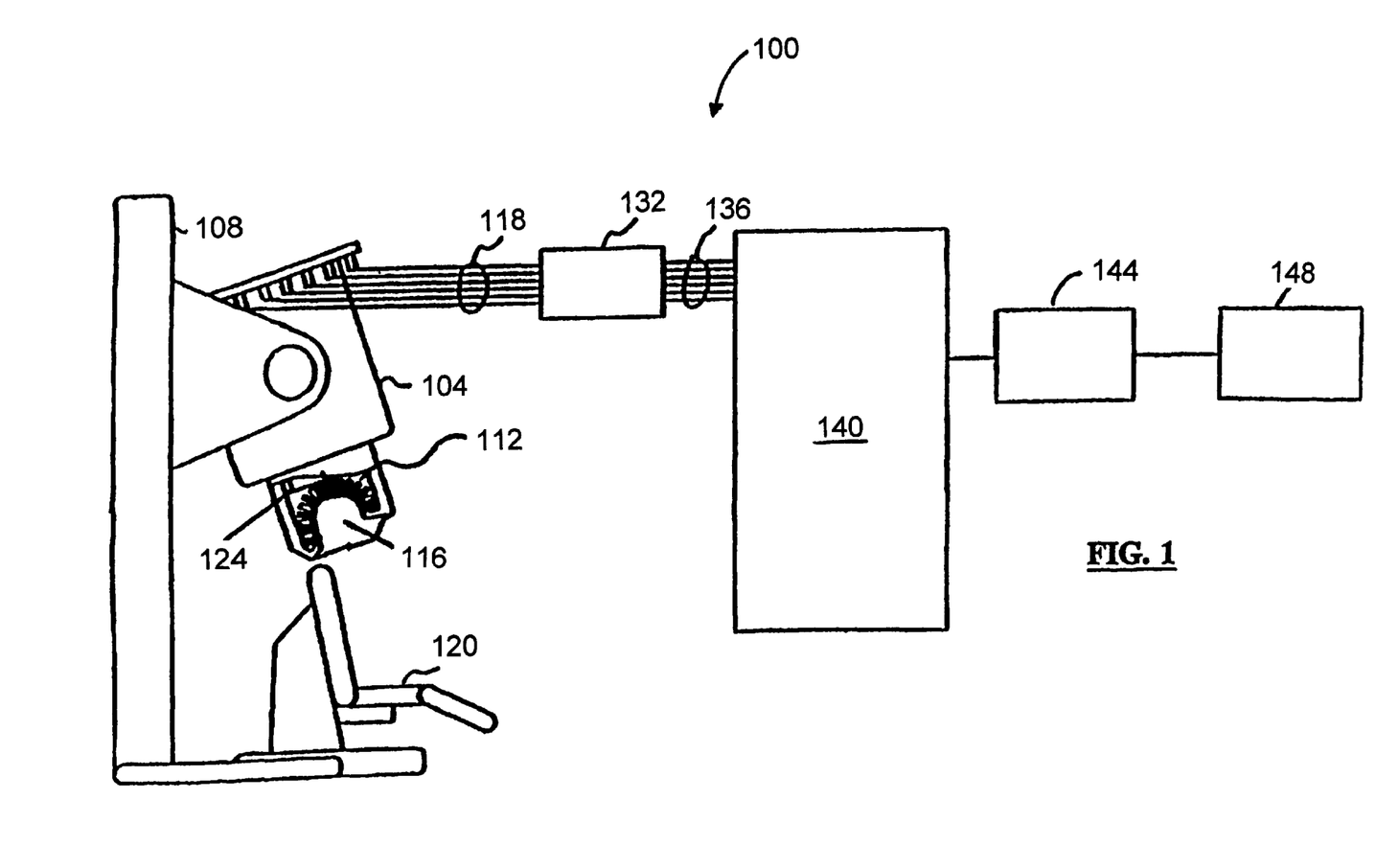
FIG. 1 illustrates a multi-channel biomagnetometer system useful to carry out the present method.

With reference to FIG. 1 there is illustrated a schematic of a 143 whole-head biomagnetometer system 100 useful for carrying out the present method. System 100 uses SQUID (acronym for "superconducting quantum interference devices") detectors and superconducting gradiometer coils for obtaining the highest sensitivity. System 100 comprises a dewar 104 which is supported by a gantry 108, the dewar having a head-shaped helmet 116 at is lower end, and a patient support 120 which supports a patient while the patient's head is inserted into helmet 116.

Dewar 104 further includes an array 112 of magnetic sensors about helmet 116 and a magnetic reference sensor system 124 above helmet 116. Array 112 of magnetic sensors may comprises gradiometer sensors, magnetometer sensors, MEG sensors and the like. The SQUIDs (not illustrated) associated with array 112 of magnetic sensors and reference sensor system 124 are located above reference sensor system 124 within dewar 104 which is filled with a cryogen (for example, liquid helium for low temperature superconductor or liquid nitrogen for high temperature superconductors) in operation, or may be refrigerated by mechanical means. As the measurements obtained from both array 112 of magnetic sensors and reference sensor system 124 are susceptible to errors due to mechanical vibration, gantry 108 is designed to minimize vibrations and to have a relatively high characteristic frequency, preferably outside the range of frequencies characteristic of brain signals. Of course, as will be understood by those of skill in the art, gantry 108 and dewar 104, with its array 112 of magnetic sensors and reference sensor system 124, can be designed with different characteristics for different sensor array and biomagnetic sources. For example, for cardiac measurements, instead of helmet 116, a different gantry and dewar that are arranged to bring the sensors proximal to the chest wall typically would be used. The design of such a system is not particularly limited and various techniques and design will occur to those of skill in the art.

In use, a set of outputs 118 from the SQUIDs associated with array 112 of magnetic sensors and reference sensor system 124 are amplified to a desired level by a SQUID pre-amplifier 132 and the resulting signals 136 are processed by System Electronics 140.

System Electronics 140 comprises a plurality of SQUID controllers and analog to digital (A/D) conversion means, to convert signals 136 to digital values of the magnetic fields and gradients measured by array 112 of magnetic sensors and reference sensor system 124, and a plurality of digital signal processors (DSPs) to perform desired processing of these digital values. The choice of DSP used in system 100 is not particularly restricted and is within the purview of a person skilled in the art.

Once processed, the resulting signals are transmitted to an Acquisition computer 144 via a suitable communications link, such as a SCSI interface and, thereafter, to a Processing computer 148 via another communications link, such as an Ethernet interface. Preferably, Acquisition computer 144 and Processing computer 148 are different computer systems, but in some circumstances they may be combined in a single computer system.

Acquisition computer 144 and Processing computer 148 can be any suitable computer systems with graphical workstation capabilities such as, for example, a suitably-equipped UNIX-based workstation or a member of the Macintosh family of microcomputers manufactured by Apple. Acquisition computer 144 performs several tasks, including tug of SQUIDs, data collection and storage and control of optional peripheral components, such as stimulus and EEG systems. Processing computer 148 performs off-line data processing of stored data and display of real time or stored data, and the results of analysis of the data. As will be apparent to those of skill in the art, processing computer 148 may also combine data from the biomagnetometer with other data, such as MRI or CAT scans, to produce graphical displays which can be interpreted in a more intuitive manner.

Additionally, EEG or other data of interest may be collected simultaneously with the measurements made by array 112 of magnetic sensors and reference sensor system 124 and, for example, system electronics 140 may include 64 additional channels to which such inputs may be applied.

Figure 2:
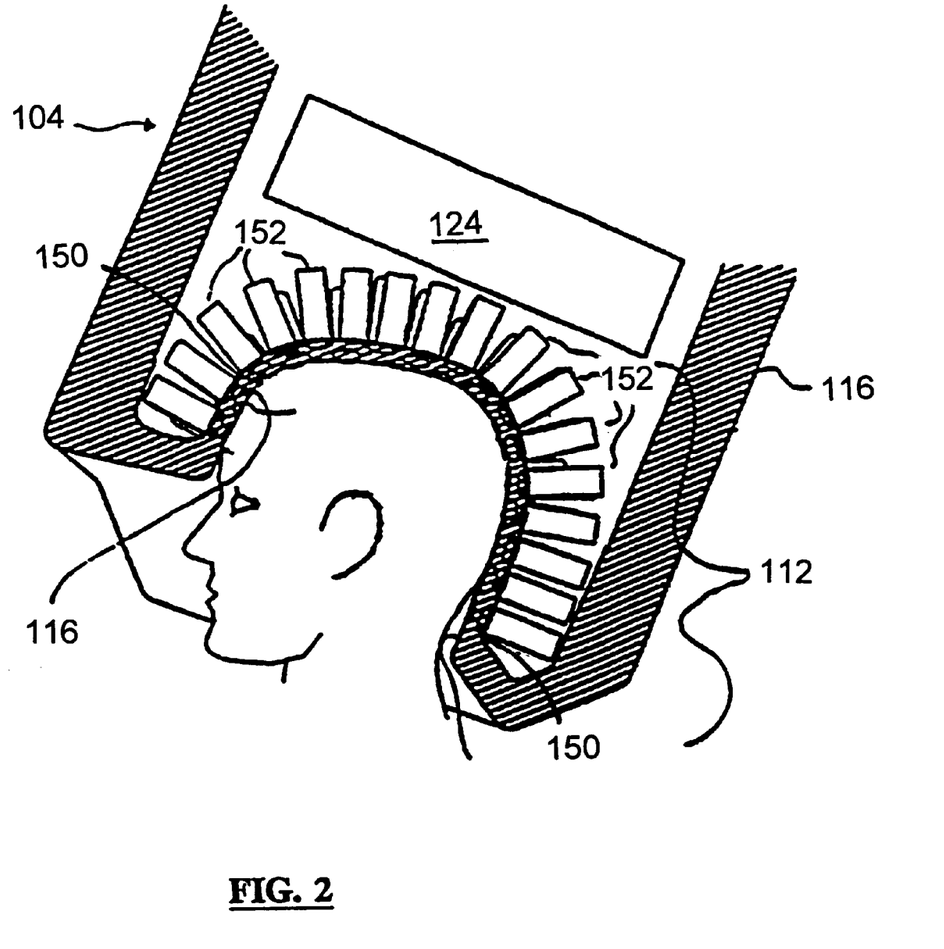
FIG. 2 illustrates a cross-section of a configuration of a helmet, array of sensors and reference system used in the biomagnetometer system of FIG. 1.

FIG. 2 illustrates helmet 116, array 112 of magnetic sensors, reference sensor system 124 and a portion of dewar 104 in more detail. As shown, helmet 116 is formed of two spaced and generally parallel walls 149,150. A series of individual sensor gradiometers 152, which make up array 112 of magnetic sensors, is disposed in a liquid helium bath adjacent parallel walls 149,150. Wall 149 is shaped to receive a human head. Helmet 116 is shaped such that each sensor 152 is located in close proximity to the surface of the human head received therein. In an attempt to ensure a good fit of helmet 116 to a variety of human heads, it has been found that different helmets can be constructed, along anthropometric lines, for biomagnetometer systems intended for use with different races.

Figure 4:
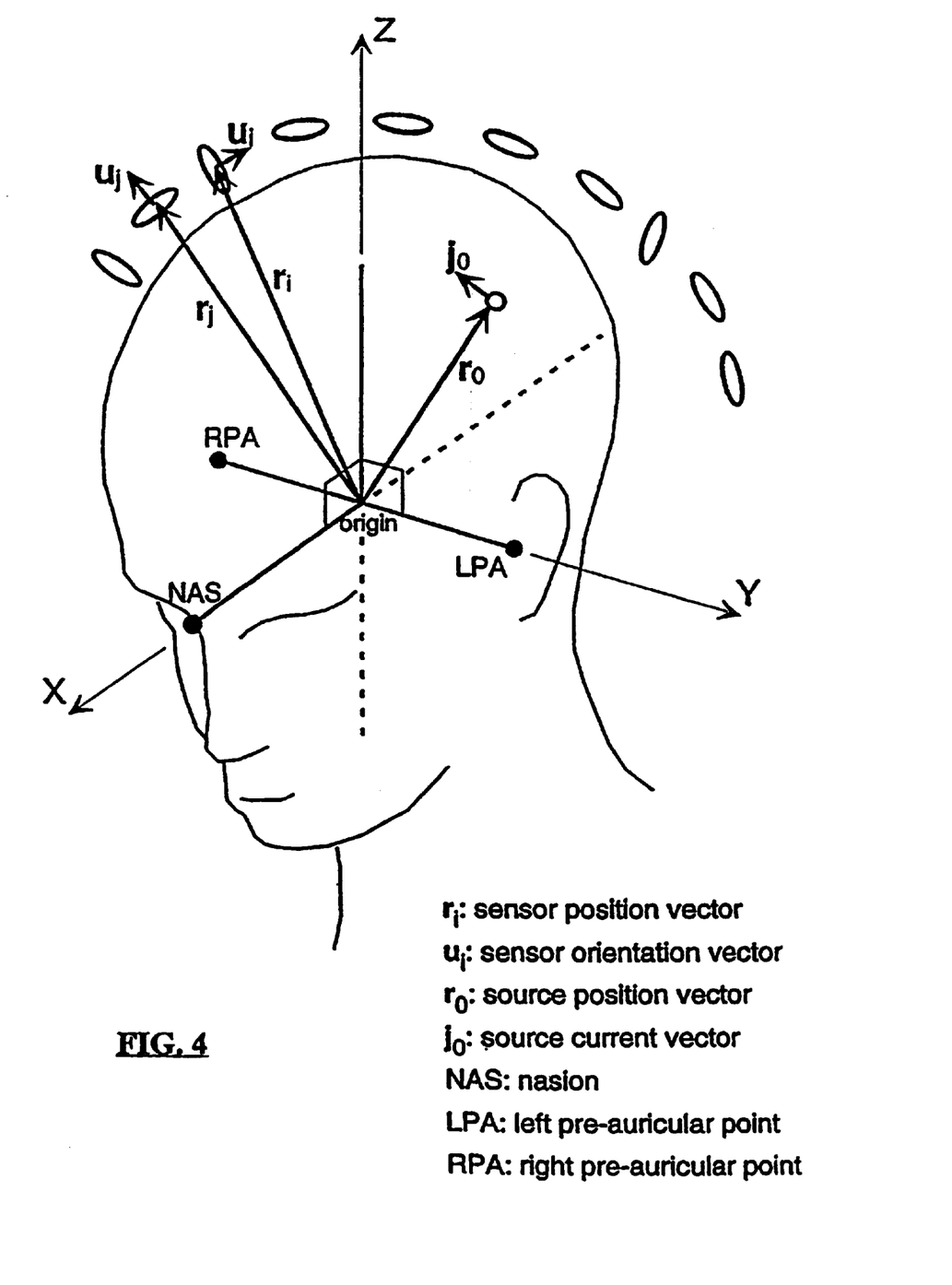

Helmet 116 is used in combination with some means of determining the head position and head frame coordinate system, relative to the sensor array. For example, a number (e.g., three) of tiny coils, also known in the art as "head coils", are affixed to a respective number of fiduciary points on the head (for example, the nasion (NAS), the left pre-auricular (LPA) point and the right pre-auricular (RPA) point as illustrated in FIG. 4), using double-sided adhesive tape. When the head coordinates are to be measured, the head coils are simultaneously energized with small AC currents, each at a different frequency, generated by digital-to-analog converters in System Electronics 140. The MEG and reference sensors are used to measure the AC magnetic fields emitted by the coils. A precise inverse solution for the positions of each of the head coils, relative to the sensor array coordinates, can then be calculated. A further head coil (i.e., a fourth if three head coils are used originally) can also be energized so that any other coordinate on the head can be determined—for example, the coordinates of EEG electrodes.

Further details on a system useful for carrying out the present method is described in published International patent application number WO 96/41209 [Vrba et al.].

Figure 3:
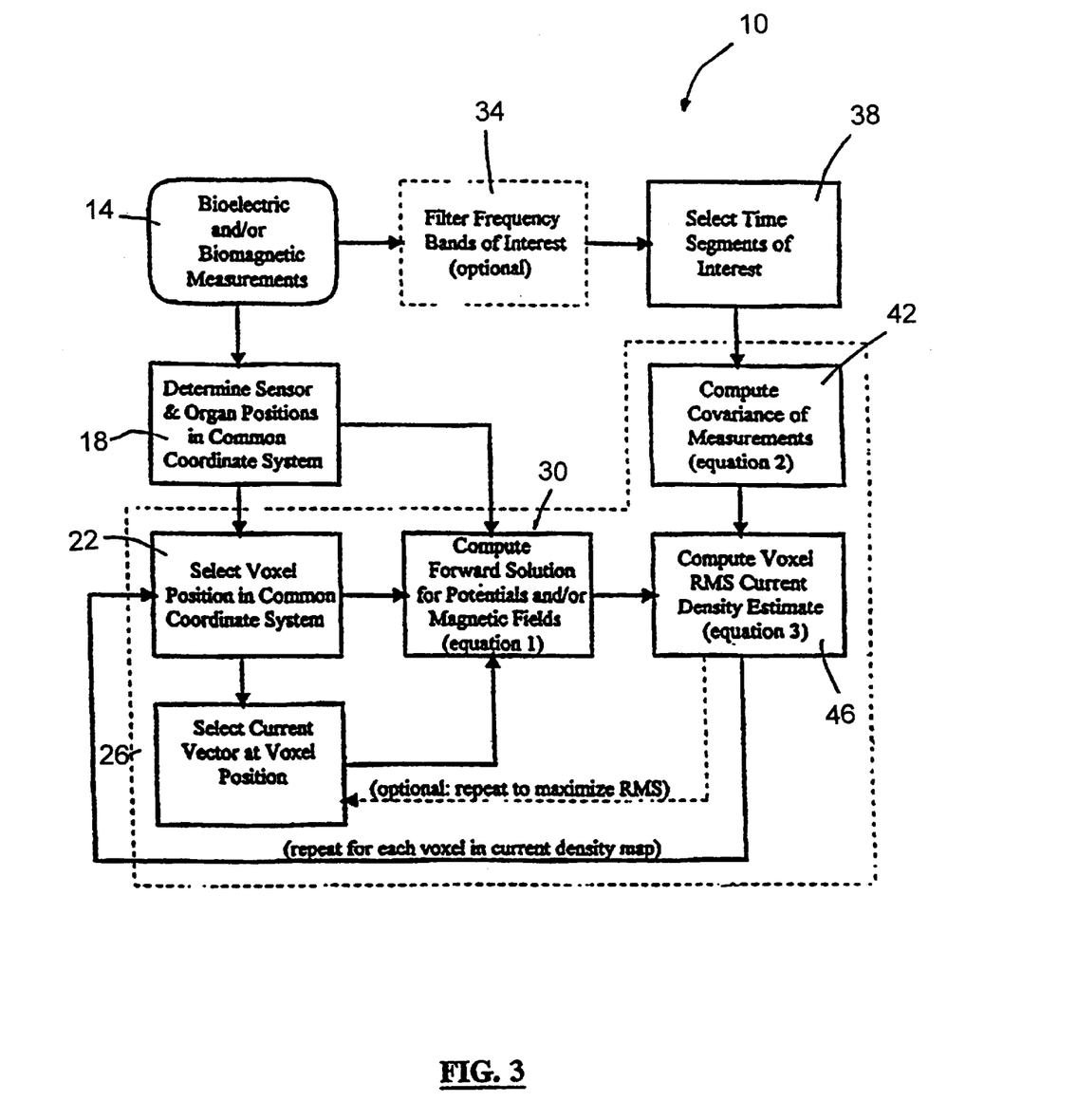
FIG. 3 is a flowchart representation of the method of one embodiment of the present invention; and, FIG. 4 is a schematic representation of the relationship between the coordinate, vector and sensor systems in the present invention.

The present method may conveniently be carried out in processing computer 148 (FIG. 1) or a supplementary computer (not shown). Referring now to FIG. 3, a flowchart representing the method of the present invention is indicated generally at 10. As indicated in FIG. 3, the first step in the method is to obtain EM signals from the organ under observation (block 14). As previously mentioned, data representing the electrical activity of the organ are measured by either biomagnetic sensors (e.g., MEG, MCG, MOG, etc.), bioelectric sensors (e.g., EEG, ECG EOG, etc.) or by both types of sensors. As will be apparent, the sensors may also include a means of detecting ambient biomagnetic and bioelectrical signals such as reference sensors, and a means of measuring the coordinates of the head relative to the sensors known as head localization (e.g., when the target organ is the brain). It is noted that for the purposes of the method of the present invention, data is measured simultaneously by the plurality of sensors in the array of sensors, optionally in combination with reference sensors. Furthermore, data is measured at discrete and regular time intervals determined by the measurement sample frequency. Further, the SAM method can be applied to any set of time samples such as for multiple intervals of time. The time interval is generally dictated by the conditions of the test and the operator, and should be of a sufficient length to enable to adequately measure at least one state of the target organ.

The precise conditions of the test will depend, at least in part, on the target organ being evaluated. For example, if the target organ is the brain, the conditions of the test may include "Object-Naming" language paradigm. In an "Object-Naming" language paradigm, a prescribed number of images (e.g., 120) of objects are presented to the subject, one image at a time. The subject is instructed to state the name of each object, as soon as it presented. For each image of object presented to the subject, the "active-state covariance" is computed (as described in detail hereinbelow) from the MEG data for a prescribed time interval (e.g., one second) prior to vocalization. For each image of object presented to the subject, the "control-state" covariance is computed (as described in detail hereinbelow) from the MEG data for a prescribed time interval (e.g., one second) after vocalization is complete. The data may therefore be divided in any logical manner to distinguish intervals of brain activity, including multiple intervals for a common state of brain activity.

In one situation, the present inventor has employed a CTF Systems, Inc.™ 143-channel whole cortex MEG system; a Hewlett-Packard model C-100 UNIX workstation was employed as a host computer for data measurement. However, as will be understood by those of skill in the art, other MEG and computing systems may be employed with similar success.

At block 18 of FIG. 3, the position of each sensor in the array of sensors is determined relative to the organ under observation. For this, both the sensors and the organ positions are referenced to a common coordinate system. As an example of the implementation of block 18, reference is made to FIG. 4, in which the organ under examination is a human brain. In the present example, wherein the above-identified whole cortex MEG system is employed, the coordinate system is established in a "head frame". In the context typical of an MEG system, the head frame is a coordinate system based upon three fiducial marks on the head (as referred to above). These are: the nasion (NAS; i.e., the indentation point where the bridge of the nose meets the forehead, and the right and left preauricular points (LPA and RPA, respectively; i.e., points that are forward of the ear canals). These landmarks are used as follows to define a coordinate system:

(i) the Y-axis is defined by the line connecting the two preauricular points;

(ii) the X-axis is defined as the line connecting the nasion with the Y-axis that is perpendicular to the Y-axis (i.e., not necessarily at the midpoint of the two pre-auricular points); and (iii) the Z-axis is defined as perpendicular to the XY-plane, at its origin.

The origin of this head frame is at the intersection of the three principal axes. Other coordinate systems, based upon other fiducial points (either internal or external) exist for the head, and may also be used, provided that they are consistent with one another. Initially, the sensor coordinates are only known within the "helmet" frame of reference. The fiducial points are measured relative to this "helmet" frame of reference. Once the positions of the fiducial points are determined, the head frame is constructed, and the sensors transformed into the head reference frame. Having a common frame of reference for the brain and the sensors is important, as the signals detected by MEG or EEG sensors depend upon the relative positions and vectors of (i) the sensors, (ii) the source generators, and (iii) the intervening conducting medium (e.g., brain, skull, scalp, etc.).

As indicated in FIG. 4, a plurality of sensors 152*a* through 152*n* are positioned in a predetermined manner about the head. As discussed above with reference to FIGS. 1 and 2, the plurality of sensors are fixed in a helmet worn by a subject such that the geometric relationship and orientation of each sensor 152 is known. A coordinate system is shown in FIG. 4, as indicated by the X, Y and Z axes, and an origin is selected as appropriate proximal a region desired for measurement. As will be understood by those of skill in the art, the coordinate system does not have to be cartesian in nature but may be any other system suitable to the particular application. As indicated in FIG. 4, the position of each of the plurality of sensors 152*a* . . . *n* can be located by a vector $r_i$ relative to the origin. The vector describing the orientation of each sensor is denoted $u_i$.

Returning now to FIG. 3, for the purpose of mapping the measured data to a voxel image array within a desired region of interest (ROI), an intervoxel spacing is selected and a grid of voxels is formed within the ROI referenced to the coordinate system (block 22). As shown in FIG. 4, any voxel position can be located by a vector $r_o$ having both a magnitude and direction from the origin of the coordinate system. Accordingly, the current vector at $r_o$ is $j_o$, corresponding to unit length current vector $n_o$. This step corresponds to block 26 in FIG. 3. The current vector at each voxel is best determined using anatomical constraints. For example, source current due to cortical activity in the brain is known to flow in a direction normal to the local cortical surface, at each point on that surface. This vector data could be obtained from an anatomical image, such as a magnetic resonance image or computed tomography (CT) of the head. This is provided that the image is translated into the common coordinate system determined for application the SAM method. In the absence of anatomical images, the current vector may be estimated by searching in u for a maximum in current density at each voxel as would be apparent to those of skill in the art.

Returning once again to FIG. 3, at block 30, the forward solution per unit source current is computed for the potential data measured by the bioelectric sensors and/or the magnetic field data measured by the biomagnetic sensors. The data measured by each sensor in the array of sensors at time sample k, neglecting sensor noise, is given by:

$$m_i(k) = \int_\Omega J(r,k) \cdot G_i(r) dv \qquad (1)$$

where J(r) is the source current distribution throughout the conductive volume of the head $\Omega$, and $G_i(r)$ is the sensitivity pattern of the $i^{th}$ sensor, also known as the Green's function. This function applies to either magnetic sensors such as a SQUID (superconducting quantum interference device) magnetometer or gradiometers, or to electrodes applied to the scalp. Equation 1 is a general expression which represents forward solutions but is not readily solved. For practical purposes, the Green's function should account for factors such as: the size and extent of the current density; the conductive medium and boundaries within which the currents flow; and, the geometry and positions of the sensors.

Practical forward solutions are known in the art. Examples of some of these published works include: a current dipole in free space (Law of Biot-Savart); a current dipole in a homogeneously conducting sphere (see, for example, *Model Studies of the Magnetocardiogram* by F. Grynzpan and D. B. Geselowitz (Biophysics Journal 13:911–925 (1973), and *Basic Mathematical and Electromagnetic Concepts of the Biomagnetic Inverse Problem* by J. Sarvas (Phys. Med. Biol. 32:11–22 (1987)); a current dipole in a homogenously conducting volume bounded by a finite mesh (see, for example, Sarvas); and a current dipole in multiple concentric spheres, each sphere having differing conductivity (see, for example, *Eccentric Dipole in a Spherical Medium: Generalized Expression For Surface Potentials* by D. A. Brody, F. H. Terry and E. Ideker (IEEE Transactions on Biomedical Engineering, BME-20:141, 143). The current dipole model generally simplifies the need for knowing the current density everywhere in space, J(r), to simply assuming it is zero everywhere except for a single point in space. With the exception of the current dipole in free space, the various previously-mentioned forward solution models make use of bounded homogeneously conducting spaces, which may have multiple compartments. Furthermore, they are a simplification of the actual medium which consists of various organs of the body and various tissue structures. At a finer level, conductivity varies rapidly, for example, between the interior of a blood vessel and the surrounding tissue. However, as the method of the present invention measures data at a macroscopic level, these effects tend to average out. Therefore, the assumption of homogeneous conductivity in each tissue compartment leads to accurate forward solutions.

Returning once again to FIG. 3, at block 34, the operator optionally filters the measured bioelectric and/or biomagnetic data into selected frequency bands of interest. Specifically, since the distribution of brain activity sometimes differs with frequency, it is useful to examine images of brain activity in specific frequency bands. Thus, ail for example, the collected data can be divided into distinct frequency bands, using a second-order digital bandpass filter. In some situations, it is preferable to filter the data for the purposes of separating artifacts due to, for example, mouth and eye movements. This filtering is also justified by the observation that somewhat different sources may appear in each frequency band.

The operator then selects at least one time window within the predetermined time interval within which the data is to be analyzed (block 38) and for which an image is to be constructed. At block 42 the optionally filtered and time segmented data is employed to compute the covariance of the measured data. Each element of the covariance matrix is given by:

$$C_{ij} = \frac{1}{K} \sum_{k=t_1}^{t_2} [m_i(k) - \overline{m}_i][m_j(k) - \overline{m}_j] \qquad (2)$$

where i,j=1,2, . . . ,M and the mean signal is computed in the conventional manner:

$$\overline{m}_i = \frac{1}{K} \sum_{k=t_1}^{t_2} m_i(k) \qquad (3)$$

The above Equation is used for calculating the covariance of the data m and is used for measured data which is both bioelectric or biomagnetic in nature. For M channels, the covariance matrix will be M×M in size. The covariance may be computed as a time integral over any time window or multiple time windows in the time interval. Covariance, for which the mean signal is removed is preferred, instead of the correlation matrix R, as real measurements may contain a DC offset which originates in the sensors and are therefore not part of the electrophysiological measurements.

At block 46 of FIG. 3, the results of blocks 30 and 42 are then combine to compute the Voxel RMS current density estimate. The mean RMS current density at any coordinate $r_o$ can then be represented by the following linear algebraic relationship:

$$\overline{J}(r_0, n_0) = \frac{1}{\sqrt{G^T(r_0, n_0)[C + \mu S]^{-1} G(r_0, n_0)}} \qquad (4)$$

where $r_o$ is the selected three dimensional coordinate, $n_o$ is the unit current vector at $r_o$ as previously described with respect to FIG. 4. C is the covariance matrix of the measurements, S is the uncorrelated sensor noise variance of all the measurements, and $\mu$ is a regularization parameter which is selected to control the trade off between noise and spatial selectivity of the current density estimate. In this matrix notation, G (without subscript) refers to the Green's functions of all sensors (i.e., G=$G_1,G_2,G_3$, . . . GM). The superscript "T" refers to the matrix transpose. Matrix and vector variables are designated by bold letters. For any given coordinate $r_o$, the vector no specifying the direction of the current, can be selected by using the vector normal to that point on the surface of the cerebral cortex, for example, extracted from a segmented MRI or CT image of the subject's brain. The results of Equation 3 is the SAM solution for the RMS current density for a voxel located at $r_o$ and having a current (unit) vector direction $n_o$.

An alternative method which is only a useful approximation is to search for the angle $n_o$ that maximizes the RMS current density at each position $r_o$.

The direct conversion of MEG and/or EEG measurements, over some designated time period, into RMS currents by Equation 3 can be seen by substituting the measurements from Equation 1 into the covariance Equation 2, the result of which is approximated by:

$$C_{ij} \approx \int_\Omega^{\overline{J^2}} (r)[G_i(r) \cdot G_j(r)]dv \qquad (5)$$

The quantity in the square brackets is conventionally referred to as the "Gram-Schmidt matrix", appearing frequently in the linear algebra of inverse problems. It is normally computed using an a priori model of all possible sources. The covariance of the measurement can be seen here to be equivalent to a Gram-Schmidt matrix that has been weighted by the mean square current density that originally gave rise to the measurement. Thus, use of the covariance obviates the need of having an a priori model of the sources to perform inverse calculations.

Normally, and preferably, spontaneous brain signals are collected, without signal averaging. The correlation or covariance matrix is computed from the signals over some time interval or intervals selected from some or all of the measured signals. Alternatively, prior to computing covariance, signals from the array may be averaged synchronously to a stimulus presented to a subject, or be triggered by an external event such as a subject pressing a switch. The stimulus may be either visual, auditory, or somatosensory.

The voxels estimating the RMS current density are then displayed, for example on a monitor, as a first image or a second image.

What is claimed is:

1. A method of performing synthetic aperture magnetometry on the signals from a target organ using an array of biomagnetic sensors positioned in a predetermined manner around a target organ, each sensor in the array having a position vector and an orientation vector relative to a common coordinate system encompassing the target organ, the method comprising the steps of:

(i) simultaneously measuring EM signals from each sensor positioned in the array for a selected time interval;

(ii) computing a covariance matrix of the measured EM signals over a user-selected time sub-interval within the selected time interval;

(iii) selecting a set of coordinates for a region of interest to be imaged and a distance between voxels to form a grid of voxels;

(iv) computing a forward solution for a current element at each of the voxels for each of the sensors in the array sensors;

(v) computing an RMS current density estimate for each voxel from the covariance matrix and the forward solution for that voxel; and (vi) displaying the voxels estimating RMS current density as a first image.

2. The method defined in claim 1, wherein the organ is a brain.

3. The method defined in claim 1, wherein the voxels are spaced to form Cartesian coordinate grid.

4. The method defined in claim 1, wherein the EM signals are magnetoencephalagraphic (MEG) signals.

5. The method defined in claim 1, wherein the EM signals are electroencephalographic (EEG) signals.

6. The method defined in claim 1, wherein the EM signals are a combination of MEG and EEG signals.

7. The method defined in claim 1, comprising, prior to Step (ii), the further Step of filtering the EM signals to a specified frequency band of interest.

8. The method defined in claim 1, wherein the further steps of repeating Steps (ii) through (vi) thereby computing a second RMS current density image over a second selected time interval and subtracting the second RMS current density image, voxel by voxel, from the first image to form a third difference image.

9. The method defined in claim 1, wherein the first RMS current density image is displayed relative to the anatomy of the organ.

10. The method defined in claim 8, wherein the second RMS current density image is displayed relative to the anatomy of the organ.

11. The method defined in claim 8, wherein the third difference image is displayed relative to the anatomy of the organ.

12. A method of performing synthetic aperture magnetometery on an electrically active organ comprising the steps of:

(i) measuring a plurality of EM data simultaneously from an array of sensors positioned around the organ;

(ii) measuring the position of an organ in a common frame of reference with the array of sensors;

(iii) computing a covariance matrix of the signals over a first selected interval of time;

(iv) selecting a set of coordinates of a region of interest to be imaged and a distance between voxels to form a grid of voxels;

(v) computing a forward solution for each sensor in the array of sensors at each of the voxels with each of the sensors current vector;

(vi) computing an RMS current density estimate for each voxel from said covariance matrix and from said forward solution for each said voxel; and (vii) displaying the voxels estimating RMS current density as a first image.

13. The method defined in claim 12, wherein the organ is a brain.

14. The method defined in claim 12, wherein the voxels are spaced to form Cartesian coordinate grid.

* * * * *